US006912913B2

(12) United States Patent
Murakami

(10) Patent No.: US 6,912,913 B2
(45) Date of Patent: Jul. 5, 2005

(54) LONG LIFE FATIGUE STRENGTH DESIGN METHOD FOR METALLIC MATERIAL

(75) Inventor: Yukitaka Murakami, Fukuoka (JP)

(73) Assignees: Kyushu TLO Company Limited, Fukuoka (JP); NSK Ltd., Tokyo (JP)

( * ) Notice: Subject to any disclaimer, the term of this patent is extended or adjusted under 35 U.S.C. 154(b) by 0 days.

(21) Appl. No.: 10/472,383
(22) PCT Filed: Mar. 11, 2002
(86) PCT No.: PCT/JP02/02281
§ 371 (c)(1), (2), (4) Date: Sep. 23, 2003
(87) PCT Pub. No.: WO02/082054
PCT Pub. Date: Oct. 17, 2002

(65) Prior Publication Data
US 2004/0112141 A1 Jun. 17, 2004

(30) Foreign Application Priority Data
Mar. 23, 2001 (JP) ........................ 2001-085347

(51) Int. Cl.$^7$ ............................................. G01N 3/32
(52) U.S. Cl. ....................................................... 73/808
(58) Field of Search ........................... 73/808, 806, 810, 73/813, 799, 789, 787, 577, 578; 420/111; 378/72; 72/53; 702/34; 428/544

(56) References Cited

U.S. PATENT DOCUMENTS 3,957,450 A * 5/1976 Salt ............................ 428/544
5,419,201 A * 5/1995 Li et al. ....................... 73/808
6,026,691 A * 2/2000 Laird et al. .................. 73/808
6,704,664 B2 * 3/2004 Su et al. ...................... 702/34

FOREIGN PATENT DOCUMENTS

JP  11-230961  8/1999

\* cited by examiner

Primary Examiner—Edward Lefkowitz
Assistant Examiner—Octavia Davis
(74) Attorney, Agent, or Firm—Wenderoth, Lind & Ponack L.L.P.

(57) ABSTRACT

A long life fatigue strength design method for a metallic material is capable of allowing design of an optimum mechanical part according to a set service life by considering an increase in ODA (area affected by hydrogen observed blackish by a metallurgical microscope) size according to the assumed service life of the mechanical part. The method includes obtaining, from the results of a fatigue test, a functional relation between the number of stress cycles to failure and the size of a hydrogen affected area around an inclusion affected by trapped hydrogen. From the functional relation, equivalent defect sizes as the sizes of the inclusions after growth corresponding to the assumed number of cycles of working stress on the mechanical part using the metallic material are obtained, and the mechanical part is designed using the equivalent defect sizes in the calculation of a long life fatigue strength such as allowable stress, whereby a failure life design can be performed with the ODA size growth taken into account according to the assumed service life of the mechanical part.

10 Claims, 5 Drawing Sheets

LONG LIFE FATIGUE STRENGTH DESIGN METHOD FOR METALLIC MATERIAL

This application is a 371 of PCT/JP02/02281.

TECHNICAL FIELD

The present invention relates to a long life fatigue strength design method for metallic material that may be used for mechanical parts such as automobile transmissions, springs and vehicle bearings that receive a significant number of cycles of stress during their service life.

BACKGROUND ART

Mechanical parts, such as automobile transmissions and vehicle bearings, receive a significant number of cycles of stress during service. Thus it is necessary to understand the number of such cycles of stress the metallic material, used for the mechanical part, will endure before service, and the metallic material should be designed based on the size, shape, service life, etc. of the mechanical parts. For metallic materials used in such mechanical parts, the fatigue limit is currently determined by considering that the material will last permanently without fatigue service if it holds up to $10^7$ incidents of stress.

In recent years, however, a newly found phenomenon exists where some materials, running out the fatigue test up to $10^7$ times, fail when they have received a stress which is lower than the fatigue limit of the conventional definition of more than $10^7$ times. The fatigue strength of a metal depends on defects present in it as well as on its intrinsic strength. Defects serve as points where stresses concentrate, providing starting points for fatigue failure. Non-metallic inclusions (hereinafter, called "inclusions") in metallic material are a type of such defects. Thus, in the conventional fatigue strength design, the stress concentration, caused by inclusions serving as fatigue failure starting points, is considered with reference to $\sqrt{(area)}$—which is the size of an inclusion expressed by the square root of its area.

Meanwhile, inclusions have the effect of trapping hydrogen in addition to stress concentration. Hydrogen, in a metal, is known to affect the microscopic failure mechanisms of the metal. This is particularly significant for high tensile steel. The fatigue area around an inclusion affected by hydrogen (i.e., the trapped-hydrogen-affected area) looks black because of its roughness when observed with a metallurgical microscope. This area is called an ODA (optically dark area). Some fatigue test results indicate that the trapped hydrogen lowers the fatigue strength of the area around an inclusion. In terms of strength, trapped hydrogen can therefore be considered to have the equivalent effect of substantially enlarging the size of inclusion.

As a result of an intensive study of trapped hydrogen by observation with the metallurgical microscopy, the ODA size is found to grow as the fatigue life is prolonged from about $10^5$ to $10^8$ times or more. The conventional fatigue strength design is, however, based on the initial size $\sqrt{(area)}$ of the inclusion. Thus, this conventional service life design is not the best model for determining the estimated service life of the mechanical part.

The present invention provides a long life fatigue strength design method for a metallic material, which can design a mechanical part best matching the estimated service life by taking into account the growth in the ODA size corresponding to the assumed service life of the mechanical part.

SUMMARY OF THE INVENTION

FIG. 1 shows the relationship between the sizes of inclusions that have trapped hydrogen and the number of cycles of stress applied to failure. The ODA area ($A_1$) around an inclusion ($A_0$) shown in FIG. 1 is the area affected by hydrogen. In FIG. 1, the size of an inclusion at fatigue fracture origin is expressed by the square root of its area, $\sqrt{(area)}$. In FIG. 1, $\sqrt{(area')}/\sqrt{(area)}$ (>1), which is the ratio of the square root ($\sqrt{(area')}$) of the sum (area') of the inclusion area and the ODA area to $\sqrt{(area)}$, is plotted as the dimensionless ODA size on the ordinate. The number of stress cycles to failure, $N_f$, is plotted on the abscissa. It is quantitatively shown in the figure that the ODA tends to grow as the number of stress cycles to failure, $N_f$, increases.

Referring to FIG. 1, the ODA size becomes larger as the cycles to failure become longer. When the number of stress cycles to failure, $N_f$, is small, or the time to failure is short, the ODA is small. This implies that a fatigue crack originates from an inclusion and grows until failure without the aid of trapped hydrogen because the applied stress is large. In contrast, when the stress is small, a crack is produced with the aid of hydrogen while receiving a great number of cycles of stress, and the crack evolution is also helped by the presence of hydrogen. After the ODA size grows large enough to grow the crack under stress without the aid of hydrogen, the fatigue crack grows, not affected by hydrogen. Thus in the area outside the ODA where the fatigue crack not affected by hydrogen grows, a fatigue fracture surface different from that seen in the ODA is formed.

In this way, the inclusion grows under repeated stress, affected by hydrogen that the inclusion itself has trapped. The equivalent defect size, which is the inclusion size after growth, increases. Thus the degree of increase in the equivalent defect size depends on both the assumed service life for the designed mechanical part, and on the assumed number of cycles of stress.

The long life fatigue strength design method for metallic material according to the present invention is a long life fatigue strength design method for metallic material including inclusions that have trapped hydrogen therearound. The method comprises: a first step of finding, based on a fatigue test, a functional relation between a number of stress cycles to failure, and a size of a hydrogen affected area around an inclusion affected by trapped hydrogen; a second step of finding an equivalent defect size, based on the functional relation, which is a size of the inclusion after growth corresponding to the assumed number of cycles of working stress on a mechanical part using the metallic material; and a third step of designing the mechanical part, using the equivalent defect size in a calculation of long life fatigue strength, such as allowable stress. Then, it becomes possible to find the equivalent defect size corresponding to the assumed number of stress cycles and to design a fatigue failure life that takes into account the ODA size growth corresponding to the assumed service life of the mechanical part.

For example, the first step is to find the functional relation based on a graph where axes are the number of cycles of stress up to failure, $N_f$, and a ratio $\sqrt{(area')}/\sqrt{(area)}$. Here, $\sqrt{(area')}$ is the equivalent defect size expressed by the square root of the sum of areas $A_0$ and $A_1$, $A_0$ being an area of the inclusion at fatigue fracture origin in the metallic material, and $A_1$ being an area of the hydrogen affected area. $\sqrt{(area)}$ is the initial size of the inclusion expressed by the square root of its area $A_0$. The second step is to find the equivalent defect size, $\sqrt{(area')}$, corresponding to the inclusion initial size, (area), by finding a corresponding value on the axis of $\sqrt{(area')}/\sqrt{(area)}$ in the functional relation, reading the assumed number of cycles of working stress on the $N_f$ axis of the graph.

Meanwhile, there are statistical fluctuations in the size of inclusions. It is the largest inclusion in the mechanical part that has a decisive impact on the fatigue strength. To estimate the size of the largest inclusion in a mechanical part, the extreme value statistics the inventor has proposed can be used. FIG. 2 illustrates the statistics of extreme value distribution of inclusions serving as starting points for fatigue failure. FIG. 2 is a diagram where data, obtained from test pieces for fatigue test, is plotted with an ordinate of accumulative count and an abscissa of inclusion size. As described earlier, inclusions act as if they grow in size with repeated stress under the existence of hydrogen. Thus the extreme value plot data is modified, considering the influence of hydrogen, based on the assumed service life. The relationship shown in FIG. 1 is used for this modification.

Namely, the long life fatigue strength design method for metallic material according to the present invention may further include a step of drawing statistics of extreme value distribution of the size of the inclusions at fatigue fracture origin in the metallic material. In the second step, it is desirable that the statistics of extreme value distribution be moved in parallel thereto based on the relationship of the equivalent defect size √(area') to the initial size √(area) of the inclusion, and it is preferable to calculate, on the moved straight line, a return period corresponding to the size and production of a real mechanical part and to then use the maximum equivalent defect size √(area')$_{max}$*, which corresponds to the largest inclusion in a real metallic material used for the mechanical part, in the estimate of allowable stress. It then becomes possible to set the equivalent defect size, corresponding to the largest inclusion in the metallic material, as the design defect size, thus allowing better design for the fatigue life.

In the design of the mechanical part in the third step, the following formula, for example, can be used that has the maximum equivalent defect size √(area')$_{max}$* as a parameter, $$\sigma = 1.56(HV/9.8+120)/(\sqrt{(area')_{max}}*)^{1/6}((1-R)/2)^\alpha$$

where σ: allowable stress (MPa) corresponding to the assumed number of cycles of working stress, HV: Vickers hardness (MPa), R: stress ratio (=minimum stress/maximum stress), and α=0.226+HV/9.8×10$^{-4}$.

For metallic materials used in such mechanical parts that receive a significant number of stress cycles, the present invention considers the influence of hydrogen trapped in the inclusion that is a defect serving as the fatigue crack starting point, and finds the maximum equivalent defect size corresponding to the size, production and design life of the real mechanical part for use in the calculation of allowable stress. It then becomes possible to ensure the safety of mechanical parts such as automobile transmissions, springs, and vehicle bearings.

DETAILED DESCRIPTION OF THE INVENTION

Now the embodiment of the long life fatigue strength design method for metallic material used for mechanical parts will be described with reference to FIGS. 3–5.

Figure 3:
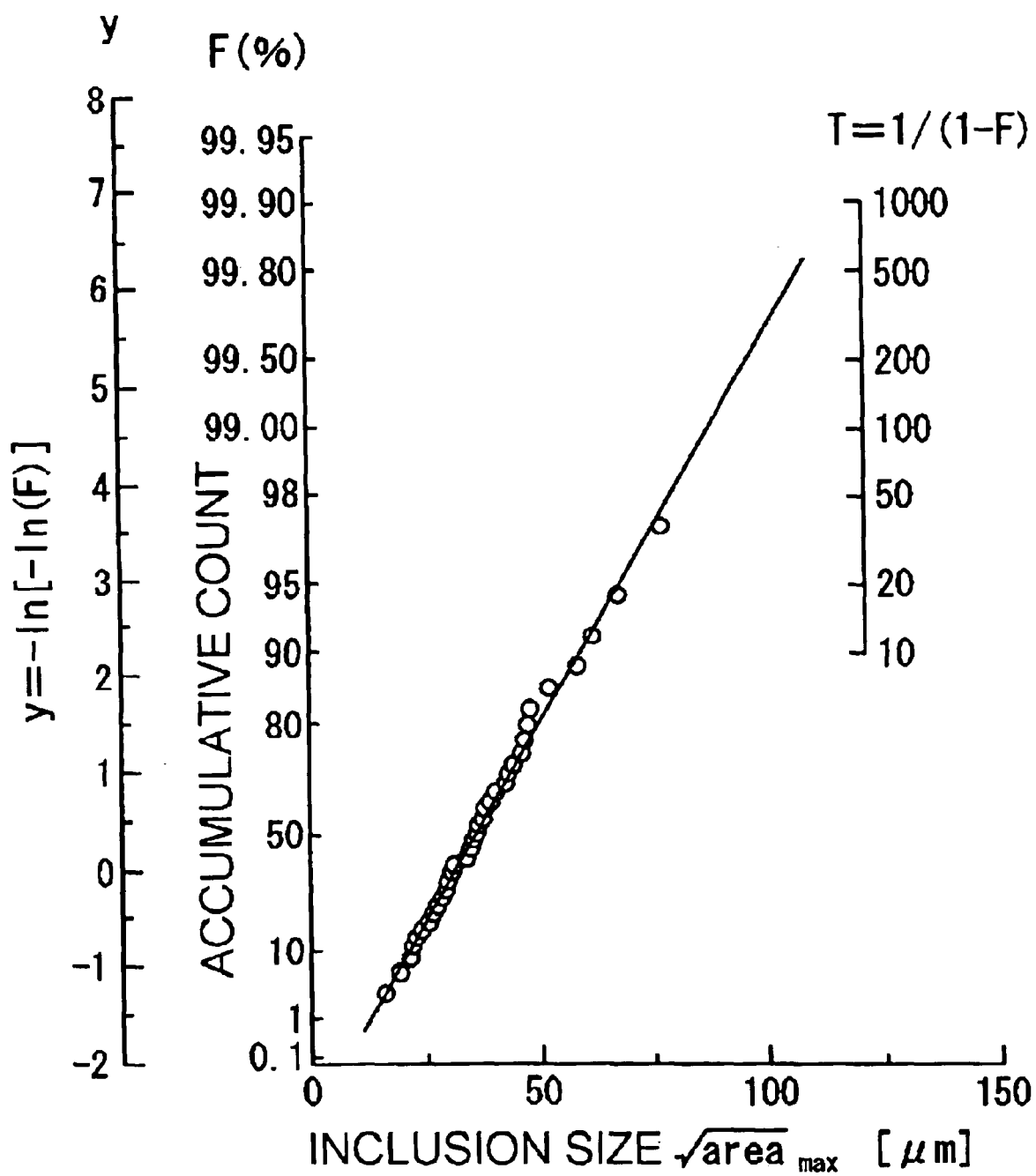
FIG. 3 is a diagram of statistics of extreme value distribution of inclusions in the material used.
Figure 4:
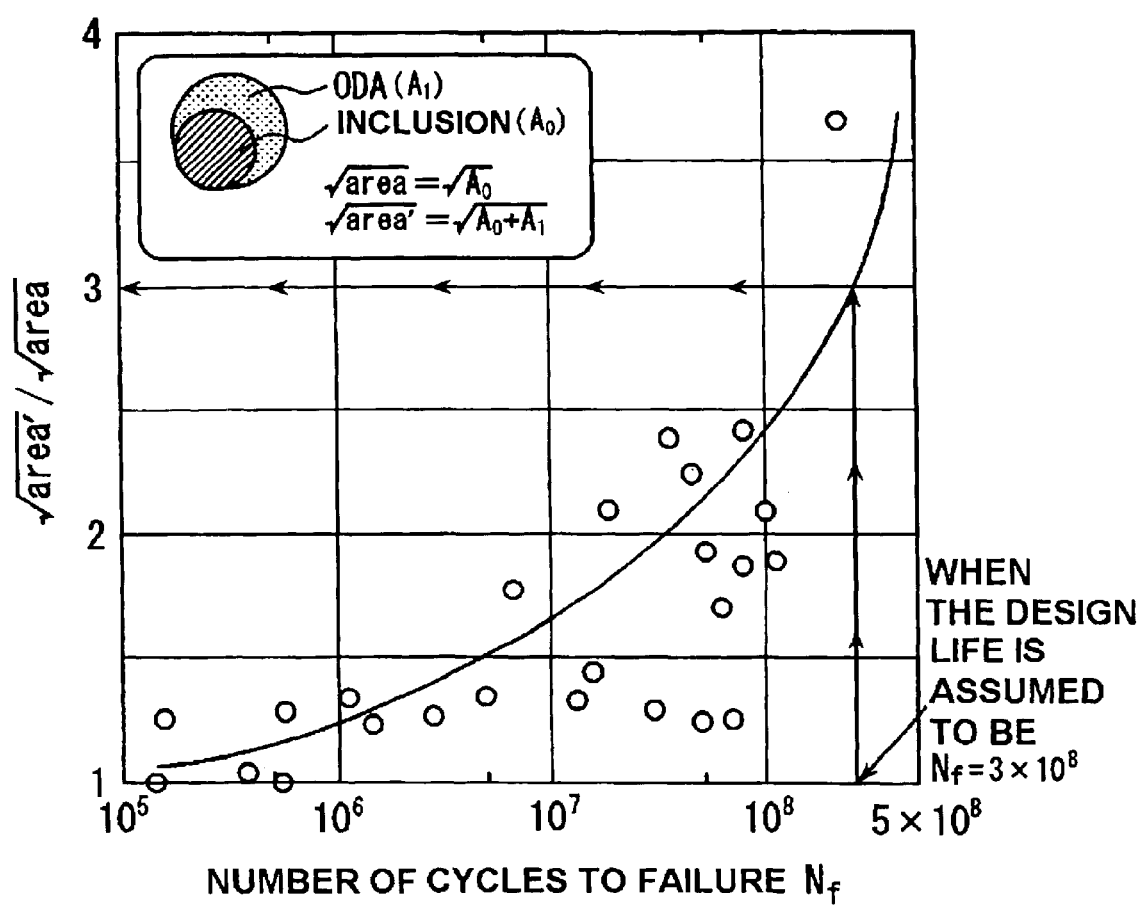
FIG. 4 is a diagram showing the relationship between the growth of the ODA and the number of stress cycles to failure.
Figure 5:
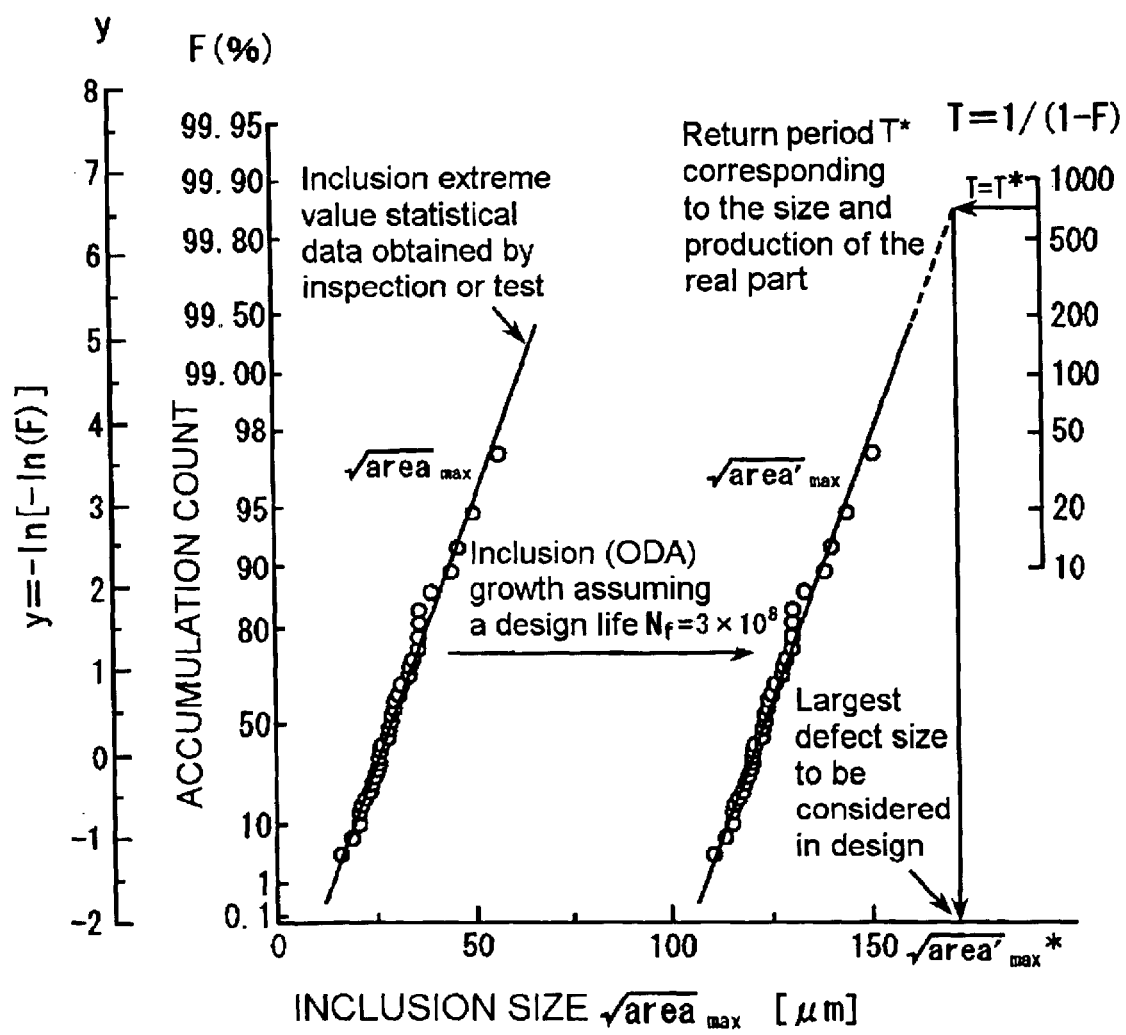
FIG. 5 is a diagram showing the steps of deciding the maximum defect size corresponding to the size, production and design life of the real mechanical part.

FIG. 3 is a diagram (graph) of statistics of extreme value distribution of inclusions in the material used, FIG. 4 is a diagram illustrating the relationship between the growth of the ODA and the number of stress cycles to failure, $N_f$, and FIG. 5 is a diagram illustrating the steps of deciding the maximum defect size corresponding to the size, production and design life of the real mechanical part.

Figure 2:
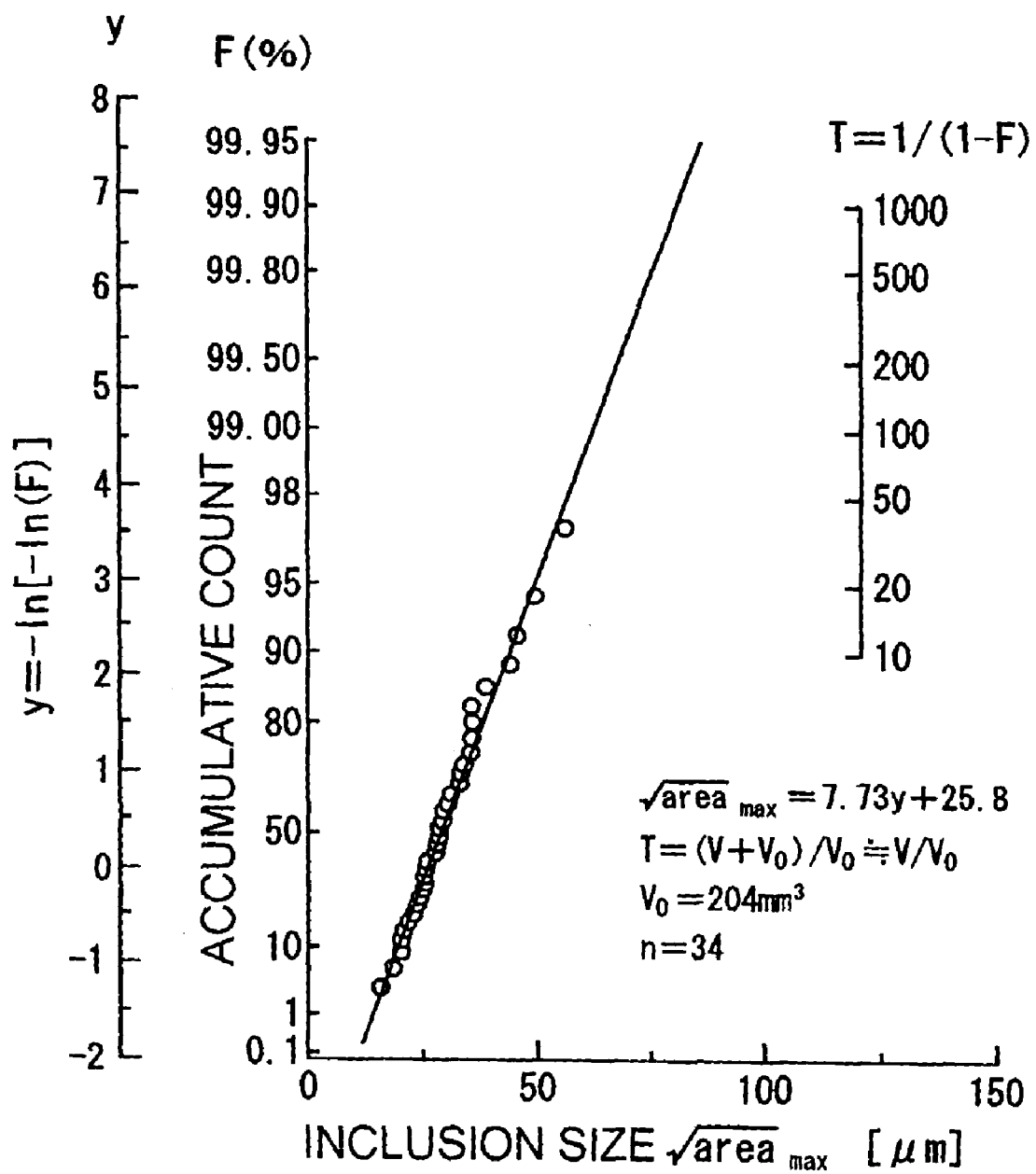
FIG. 2 is a diagram showing the statistics of extreme value distribution of inclusions at fatigue fracture origins.

The first step is to conduct a fatigue test using test pieces of the metallic material to be used in the mechanical part to be designed. As shown in FIG. 3, a diagram is drawn of statistics of extreme value distribution like FIG. 2 for inclusions in the used material, with the accumulative count plotted on the ordinate and the inclusion size plotted on the abscissa.

Figure 1:
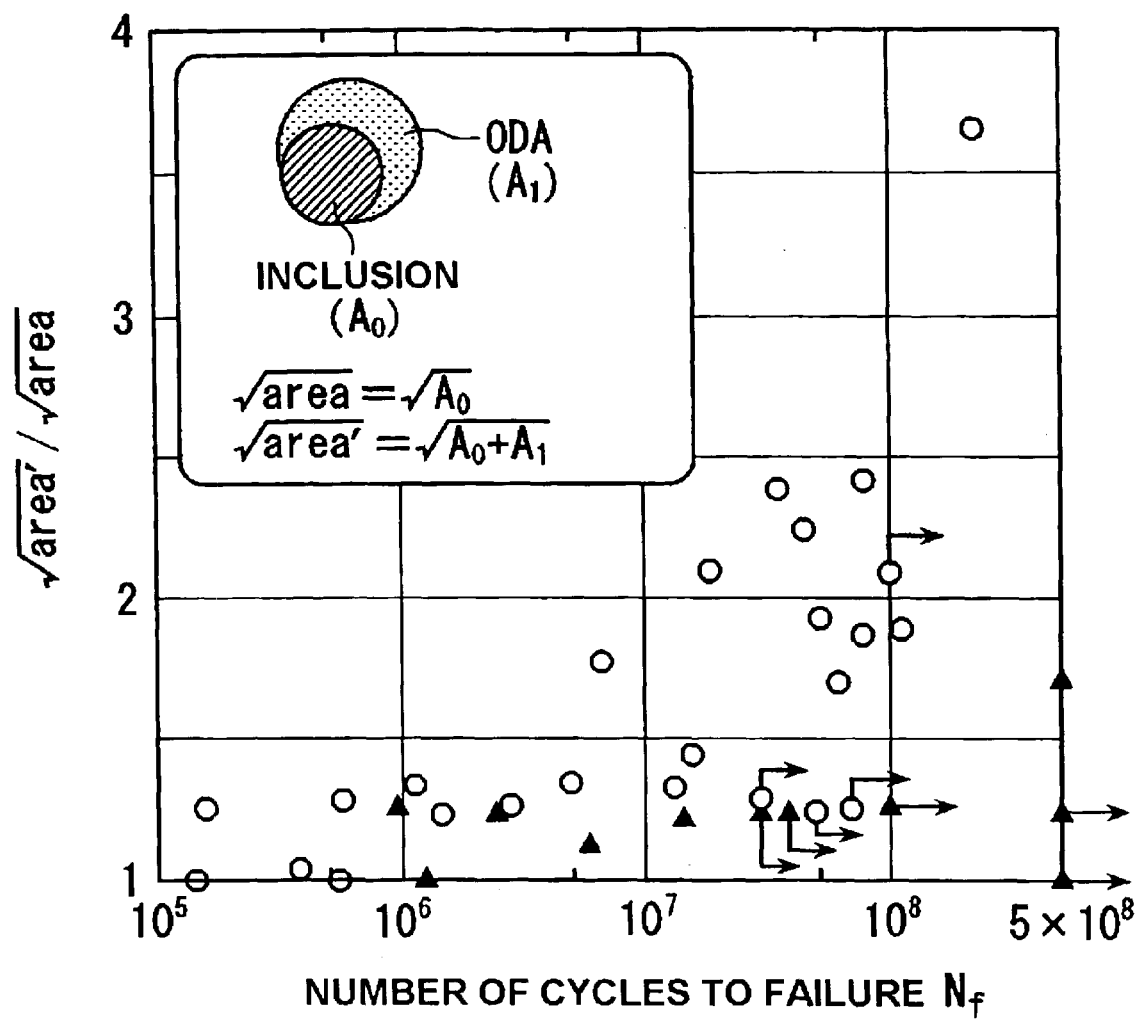
FIG. 1 is a diagram showing the relationship between the sizes of inclusions that have trapped hydrogen and the number of stress cycles to failure.

In this fatigue test, the functional relation between the number of stress cycles to failure, $N_f$, and the dimensionless ODA size (√(area')/√(area)) around the inclusion affected by hydrogen is found, as shown in FIG. 4. The dimensionless ODA size is the ratio of the inclusion size √(area), expressed by the square root of the inclusion area, $A_0$, to a size (area') which is the square root of the sum of the area, $A_0$, of the inclusion serving as a fatigue fracture origin and the ODA area, $A_1$. FIG. 1 may be used as an approximation applicable to many materials. Note that, however, the curves obtained by the plots in FIG. 1 change with the hydrogen content in the metallic material.

Using FIG. 4, the equivalent defect size √(area') that is the inclusion size after growth corresponding to the assumed number of cycles of working stress on the mechanical part is found. For example, assuming $N_f=3\times10^8$ on the abscissa of FIG. 4, the corresponding √(area')/√(area) is about 3. Then the equivalent defect size √(area') is estimated to be three times the initial size √(area) of the inclusion. However, the real mechanical part is larger than the test pieces and has inclusions much larger than those found by experiment. Thus, in order to estimate their sizes, the data of FIG. 3 is moved to the right in parallel thereto and according to the assumed number of cycles of use of the mechanical part (see FIG. 5), and a return period T=T* is calculated on the moved straight line in accordance with the size and production of the real mechanical part to find the maximum equivalent inclusion size, √(area')$_{max}$*, of the largest inclusion expected to be included. Namely, adopt this maximum equivalent inclusion size √(area')$_{max}$* as the maximum equivalent defect size corresponding to the size, production, and design life of the real mechanical part.

When using the equivalent defect size √(area') in the calculation of allowable stress, the following √(area) parameter model, for example, which the inventor has already suggested, can be used.

$$\sigma = 1.56(HV/9.8+120)/(\sqrt{(area')})^{1/6}((1-R)/2)^\alpha$$

where σ: allowable stress (MPa) corresponding to the assumed number of cycles of stress in design, HV: Vickers hardness (MPa), R: stress ratio (=minimum stress/maximum stress), and α=0.226+HV/9.8×10$^{-4}$. Then, the maximum equivalent defect size √(area')$_{max}$* (μm) including the ODA determined above is entered as the equivalent defect size √(area'), and the allowable stress (MPa) corresponding to the assumed number of cycles of working stress in design is calculated.

When using another design formula instead of the above one, safety is not ensured unless the fatigue strength design takes into account the above equivalent defect size √(area') (maximum equivalent defect sizes √(area')$_{max}$*). For example, in the conventional method that determines the allowable stress corresponding to the assumed number of cycles in service based on the test results of a few test pieces or the real part, the influence of the largest inclusion included in many parts is not considered, or the influence of crack growth from the inclusion initial size affected by hydrogen is not considered. Thus, fatigue strength reliability is not ensured.

As mentioned thus far, it becomes possible to design a failure life that takes into account the ODA size increase corresponding to the assumed service life of the mechanical part by: finding the functional relation between the number of cycles of stress to failure, $N_f$, and the size of the hydrogen affected area around inclusion affected by trapped hydrogen, √(area')/√(area), based on a fatigue test; finding the equivalent defect size as the size of each inclusion after growth corresponding to the assumed number of cycles of working stress; and designing the mechanical part using the equivalent defect sizes for the calculation of a long life fatigue strength such as allowable stress.

INDUSTRIAL APPLICABILITY

The present invention is useful as a long life fatigue strength design method applicable to metallic material used in mechanical parts such as automobile transmissions, springs and vehicle bearings that receive a significant number of cycles of stress during their service life.

What is claimed is:

1. A long-life fatigue strength design method for a mechanical part to be made of a metallic material, comprising:

determining a functional relationship between a number of stress cycles to failure and a size of a trapped-hydrogen-affected area around a non-metallic inclusion in the metallic material, said determining of the functional relationship being based on a fatigue test performed on a portion of the metallic material;

determining an equivalent defect size, the equivalent defect size being a size of the non-metallic inclusion after growth corresponding to an assumed number of working stress cycles on a mechanical part to be made of the metallic material, said determining of the equivalent defect size being based on the determined functional relationship; and designing the mechanical part by using the equivalent defect size in a calculation of an ultra-long life fatigue strength.

2. The method of claim 1, wherein:

said determining of the functional relationship comprises preparing a graph illustrating the functional relationship, the graph having:

a first axis indicating the number of stress cycles to failure, $N_f$; and a second axis indicating a ratio √(area')/√(area), wherein √(area') is the equivalent defect size expressed by the square root of the sum of areas $A_0$ and $A_1$, in which $A_0$ is an area of the non-metallic inclusion in the metallic material at fatigue failure origin, in which $A_1$ is an area of the trapped-hydrogen-affected area, and in which √(area) is an initial size of the non-metallic inclusion expressed by the square root of area $A_0$; and said determining of the equivalent defect size comprises determining the equivalent defect size, √(area'), corresponding to the inclusion initial size, √(area), by finding on the graph a value on the second axis corresponding to the assumed number of working stress cycles on the first axis.

3. The method of claim 2, further comprising:

preparing a second graph of statistics of extreme value distribution of sizes of the non-metallic inclusions at fatigue failure origins in the metallic material; and wherein said determining of the equivalent defect size includes moving the line of the second graph of statistics of extreme value distribution in parallel thereto based on a relationship between the equivalent defect size √(area') and the inclusion initial size √(area), so as to calculate a return period corresponding to a size of the mechanical part on the moved parallel line; and said designing of the mechanical part comprises using a maximum equivalent defect size √(area')$_{max}$* of a largest non-metallic inclusion in the metallic material to be used in the mechanical part in an estimate of allowable stress.

4. The method of claim 3, wherein the metallic material is high tensile steel.

5. The method of claim 3, wherein said designing of the mechanical part comprises using a formula having the maximum equivalent defect size √(area')$_{max}$* as a parameter, the equation being as follows:

$$\sigma = 1.56(HV/9.8+120)/(\sqrt{(area')}_{max}*)^{1/6}((1-R)/2)^\alpha$$

wherein: σ is the allowable stress (MPa) corresponding to the assumed number of cycles of working stress; HV is the Vickers hardness (MPa); R is the stress ratio (=minimum stress/maximum stress); and α=0.226+HV/9.8×10$^{-4}$.

6. The method of claim 5, wherein the metallic material is high tensile steel.

7. The method of claim 2, wherein said designing of the mechanical part comprises using a formula having the maximum equivalent defect size √(area')$_{max}$* as a parameter, the equation being as follows:

$$\sigma = 1.56(HV/9.8+120)/(\sqrt{(area')}_{max}*)^{1/6}((1-R)/2)^\alpha$$

wherein: σ is the allowable stress (MPa) corresponding to the assumed number of cycles of working stress; HV is the Vickers hardness (MPa); R is the stress ratio (=minimum stress/maximum stress); and α=0.226+HV/9.8×10$^{-4}$.

8. The method of claim 7, wherein the metallic material is high tensile steel.

9. The method of claim 2, wherein the metallic material is high tensile steel.

10. The method of claim 1, wherein the metallic material is high tensile steel.

* * * * *